United States Patent
Goldschmied

[11] Patent Number: 6,139,317
[45] Date of Patent: Oct. 31, 2000

[54] ORTHODONTIC APPLIANCE

[75] Inventor: Felix Goldschmied, Launceston, Australia

[73] Assignee: Goldschmied Proprietary Ltd., Tasmania, Australia

[21] Appl. No.: 09/051,699

[22] PCT Filed: Oct. 17, 1996

[86] PCT No.: PCT/AU96/00651

§ 371 Date: Apr. 16, 1998

§ 102(e) Date: Apr. 16, 1998

[87] PCT Pub. No.: WO97/14370

PCT Pub. Date: Apr. 24, 1997

[30] Foreign Application Priority Data

Oct. 17, 1995 [AU] Australia .............. PN 5977

[51] Int. Cl.⁷ .................................. A61C 3/00
[52] U.S. Cl. ........................... 433/14; 433/11
[58] Field of Search ................... 433/11, 14

[56] References Cited

U.S. PATENT DOCUMENTS

| | | | |
|---|---|---|---|
| 3,085,335 | 4/1963 | Kesling | 32/14 |
| 3,085,336 | 4/1963 | Kesling | 433/14 |
| 3,435,527 | 4/1969 | Kesling | 433/14 |
| 3,445,933 | 5/1969 | Kesling | 32/14 |
| 3,780,437 | 12/1973 | Wildman | 32/14 |
| 4,026,022 | 5/1977 | Paugh et al. | 433/14 |
| 4,180,912 | 1/1980 | Kesling et al. | 433/13 |
| 4,209,906 | 7/1980 | Fujita | 433/11 |
| 4,260,375 | 4/1981 | Wallshein | 433/11 |
| 4,350,487 | 9/1982 | Kesling et al. | 433/14 |
| 4,355,975 | 10/1982 | Fujita | 433/11 |
| 4,496,318 | 1/1985 | Connelly, Jr. | 433/14 |
| 4,585,413 | 4/1986 | Wool | 433/8 |
| 4,639,219 | 1/1987 | Gagin | 433/22 |
| 4,676,747 | 6/1987 | Kesling | 433/18 |
| 4,941,825 | 7/1990 | Lerner | 433/14 |
| 5,356,288 | 10/1994 | Cohen | 433/8 |
| 5,362,233 | 11/1994 | Thompson | 433/14 |

*Primary Examiner*—John J. Wilson
*Attorney, Agent, or Firm*—Ladas & Parry

[57] ABSTRACT

An orthodontic appliance including: bracket (101) having a substantially flat base (102) for engaging a tooth, and a securing member (103); and facia (110) able to engage with the securing member (103) to form part of the bracket (101); wherein the combination of the facia (110) and the securing member (103) forms a slot within the bracket (101), able to receive a pin (114) and secure the pin in position.

23 Claims, 12 Drawing Sheets

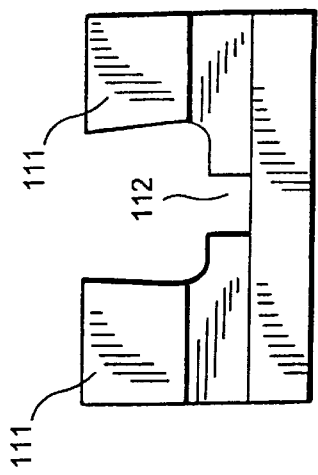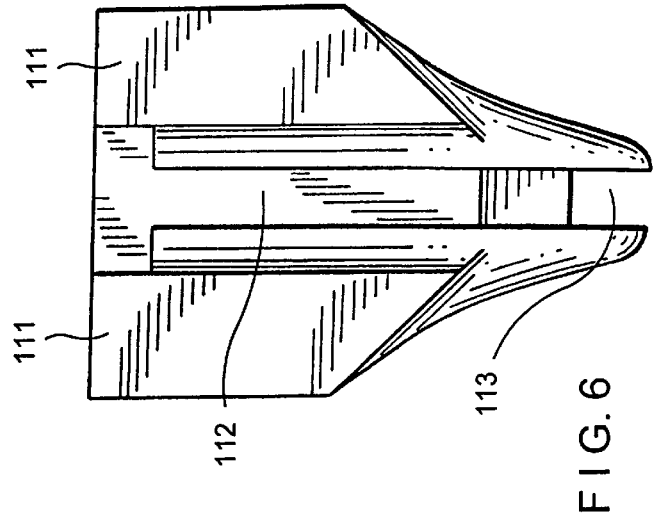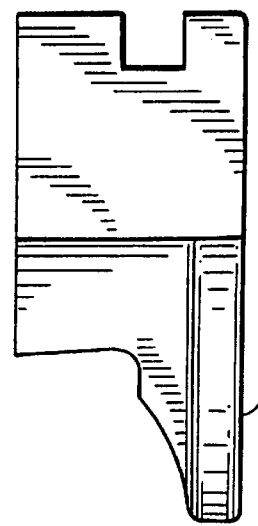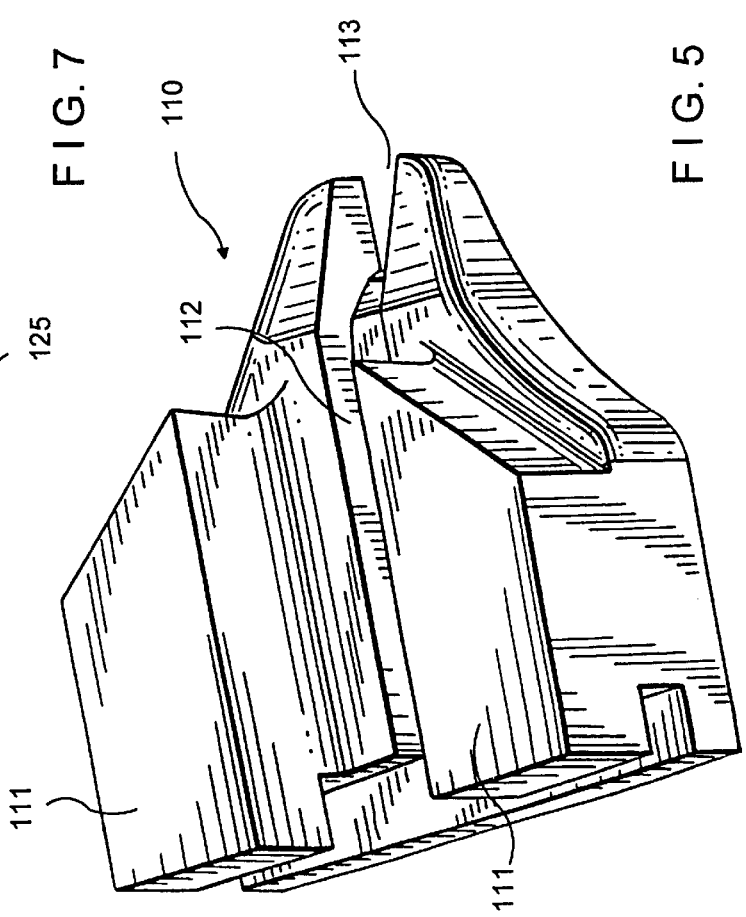

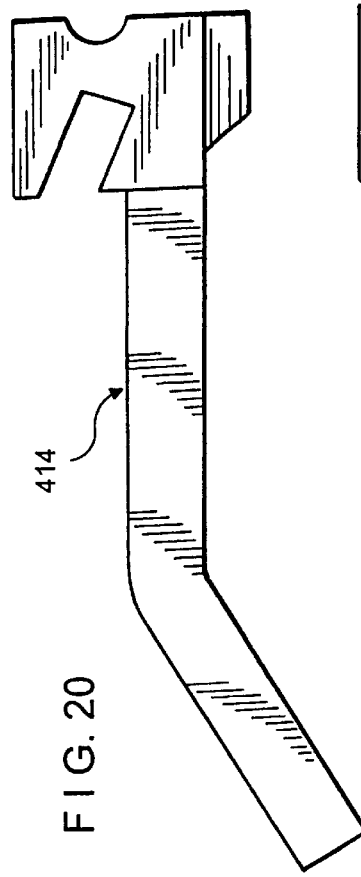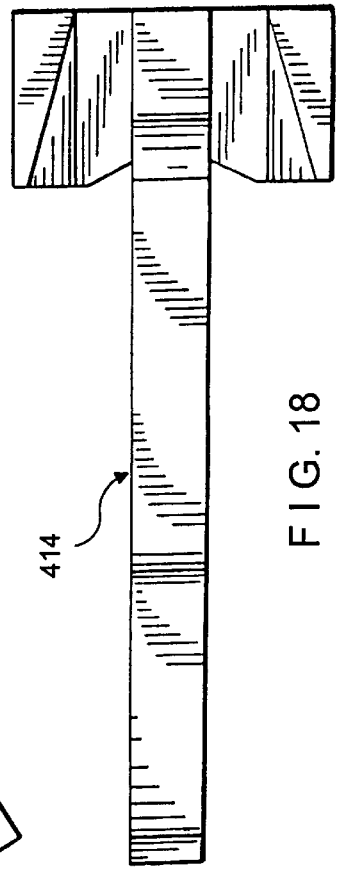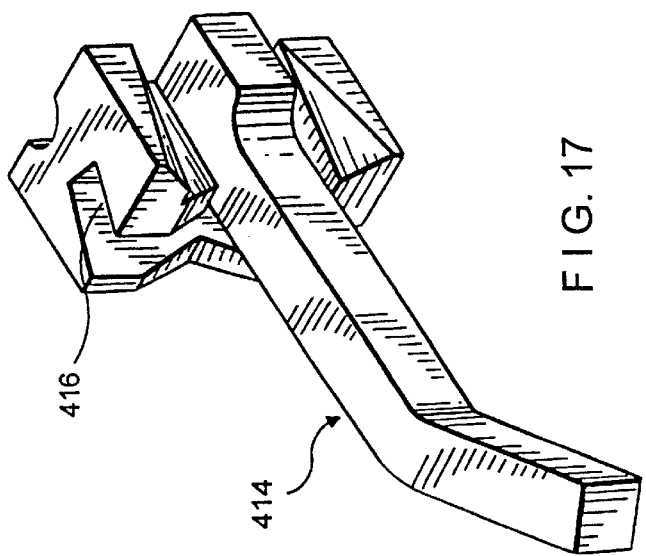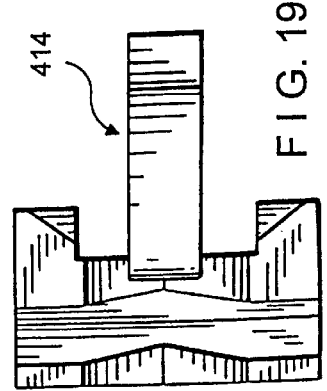

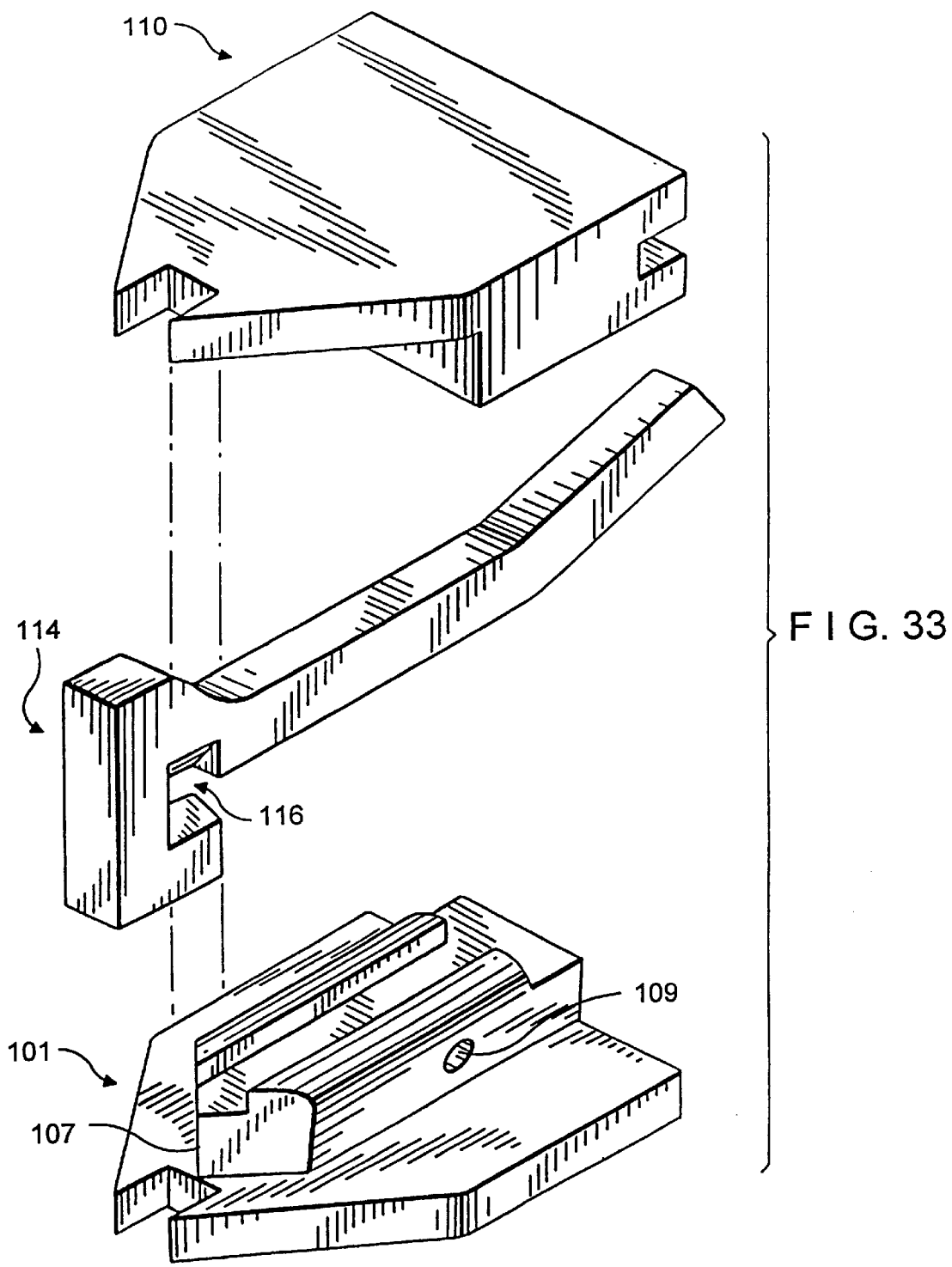

ORTHODONTIC APPLIANCE

This invention relates generally to the field of orthodontics and in particular to a novel orthodontic appliance, including a bracket and a securing member, the combination of which is able to accommodate a series of pins. The invention also relates to a technique of utilising such an appliance.

The field of orthodontics generally applicable to the present invention, involves appliances and techniques relating to the application of appliances to teeth in order to straighten or in some manner move the teeth within the mouth. Treatment with such appliances are generally for cosmetic or other functional purposes.

The most commonly used techniques involve the use of brackets which are affixed to the tooth surface, and archwires which are held in position by the brackets. Correct manipulation of the archwire and the bracket, allows the operator to apply forces upon a tooth in an attempt to cause movement. Various techniques have developed utilising differing brackets and archwires in order to provide orthodontic treatment. One such technique is the Begg technique which involves the gentle free tipping movement of the teeth. The teeth may be moved into existing spaces or spaces created by extracting strategic teeth. Other techniques utilise Edgewise brackets and variations of the Edgewise bracket in order to induce movement of teeth.

A bracket is a device that is generally attached either directly to the tooth or by means of a band surrounding the tooth and may include a horizontal projection to support an archwire. Generally, the appliances used in current techniques utilise brackets and an archwire. The archwire is generally secured to the bracket by means of ligatures, or by the use of pins or other holding devices. The archwire may be secured within the bracket or received between the bracket surface and the inside of the bracket and held firmly against the inside of the bracket.

Appliances that are used in orthodontic treatments are classified generally according to their surface application. Such appliances include labial and buccal, utilising appliances that are applied to the outer surface of the tooth; lingual and palately utilising appliances affixed to the interior surface of the tooth, or labialingual applied to both surfaces. Generally, the Edgewise technique is a labial and buccal arch technique that allows for suitable control in the labiolingual, mesiodistal and gingival directions. In the Edgewise appliance, a round or rectangular archwire is layed flat against the labial/buccal surface of the tooth. The archwire is shaped and affixed into a support in the brackets.

The Edgewise bracket has a rectangular cross sectioned support into which the archwire fits, and wings for tying the archwire with some form of affixation. The support may be single, double or treble, and may be straight or angulated in order to provide torque to the tooth. With such brackets, the width of the attachment is important, since this is what allows control of the movement of tooth in the mesiodistal direction. Other types of brackets such as the begg bracket utilise a pin to secure the archwire rather than affixations. Auxiliaries such as uprighting springs, rotational springs and torquing arches are used to empirically drive the teeth into their desired position.

Ceramic and plastic brackets have also been used in the Begg and various alternatives of the Edgewise technique. With the Begg bracket technique, the ceramic brackets are tending to fracture due to the fine nature of the bracket design or dilaminate from the bases to which they adhere to. Stainless steel and titanium wires also have a detrimental effect upon ceramic brackets causing fracture of brackets and wear. Plastic brackets have generally been discarded, as they readily distort.

In the Edgewise techniques the width and depth of a bracket slot are critical and thus any excessive wear is detrimental to good treatment. Once the brackets are placed on a tooth they can not be easily interchanged and as such, once the bracket slot is worn, or damaged, the treatment-is effected. This applies to both the Begg and Edgewise techniques. The ceramic Edgewise bracket is also prone to fracture and is generally bulky.

The present invention aims to overcome or at least alleviate one or more of the difficulties associated with the prior art.

According to a first embodiment, the present invention resides in an orthodontic appliance including:

a bracket having a substantially flat base for engaging a tooth, and a securing member having a V-shaped terminal aspect, a facia, able to engage with the securing member to form part of the bracket; and a pin having an appendage including a recess having an active surface;

wherein the combination of the facia and the securing member form a channel within the bracket, able to secure the pin in a position where a slot is formed between the V-shaped terminal aspect of the securing member and the recess, and said pin is able to retain longitudinal movement.

In a second embodiment, the present invention resides in an orthodontic appliance including:

a bracket having a substantially flat base for engaging a tooth, a securing member having a V-shaped terminal aspect, and a pin having an appendage including a recess having an active surface;

wherein the combination of the base and the securing member form a channel, able to secure the pin in such a position where a slot is formed between the V-shaped terminal aspect of the securing member and the recess; and said pin is able to retain longitudinal movement.

The pin forms part of the orthodontic appliance of the invention and is the active component of the appliance in that it provides the mechanics of the slot. The pin generally consists of a stem, and an appendage which includes a recess having at least one active surface. The pin is adapted to be secured within the channel formed between the bracket and the securing member of the orthodontic appliance, in such a manner so as to prevent rotation, but allow for longitudinal movement of the pin.

During treatment, the pin may be replaced, and a number of different pins may be used, each having a different active surface or surfaces, to apply a different treatment upon a tooth. The active surface or surfaces of the pin, in conjunction with an archwire, is able to apply a prescribed force upon a tooth of a patient. Generally the applied force is torque or angulation.

A different type of pin may be used on different teeth at any one time. A specific pin may be manufactured and utilised for the appliance depending upon the treatment. During the treatment of a patient, a plurality of different pins may be used within a particular appliance through the course of treatment.

The base of the bracket may be considered to be substantially flat. However the base may have some curvature to account for the shape of the surface of the tooth. The term "substantially flat base" includes within its scope, the variations applicable to account for the shape of the surface of a tooth. The base may also be angulated to provide some torque to the tooth.

Most preferably, the facia, if present, is a separate unit, that is compatible with the securing member of the bracket. However, it is possible that the facia is formed integrally with the securing member and so formed to allow for a channel that is able to house the pin. In this form, the channel is formed between the base and the securing member, without the need for a separate facia. Indeed, the base and the securing member may also be integral with each other.

In the first embodiment of the invention, the securing member of the bracket may form a tongue arrangement that is compatible with a groove formed within the facia, forming a sleeve to secure over the tongue. The facia is generally secured to the bracket by the configuration of the sleeve and the securing member. Preferably, the facia also includes a centrally located channel, however, a channel may be formed in only one of the securing member or the facia. It is not critical whether the channel is formed in either the securing member, facia or both, however when the facia is secured over the securing member, a channel should be formed between these components when they are placed together. The channel should be of such dimension so as to readily receive, and lock the pin into position, so that it cannot rotate, but may move in a longitudinal direction.

The channel is the passive factor in the mechanisms and the pins are the active aspect of the appliance. The slot formed between the appendage and the V-shaped terminal aspect is able to open and close during treatment, due to combined forces causing longitudinal movement of the pin.

Rotation is generally prevented if the pin has the same cross section as the channel. The pin and the channel may have for example a square or rectangular cross section. The appliance may also be ligated, or a C clamp or alternatively, a spring or elastic may be used to assist in maintaining the pin in the bracket channel. The C clamp or alternatives may be used with all techniques and at any time after the arch wires are seated firmly in the bracket, they may be used during a tip control procedure and whilst uprighting, with no uprighting springs or auxiliaries required.

In use, the pin in the orthodontic appliance preferably faces gingivally with the appendage facing occlusally, and the V-shaped terminal aspect of the securing member facing occlusally. Preferably, the pin includes an auxiliary groove on the occlusal surface of the appendage. An elastic, spring or alternative auxiliary may be used to hold the pin in position, where the elastic or other auxiliary is placed in the auxiliary groove on the appendage, and around the stem of the pin to hold it within the securing member. The pin still retains longitudinal movement that may act against the forces of the elastic or other holding devices.

Alternatively, or in addition, an auxiliary channel may also run longitudinally between the pin and the flat base. A spring may be used to hold the pin in position. Both the elastic and the spring are positioned to apply some force on the pin to hold the appendage against the V-shaped terminal aspect. Due to combined forces which may be applied to the pin, the pin will tend to actively move against the forces of the auxiliary, moving in a longitudinal direction, with the auxiliary tending to drive the pin back into position. The pin, in effect may act in a piston motion.

It is a further feature that the securing member includes a V shaped terminal aspect, having a sharp edge, such that the contact between the archwire and the securing member is a sharp edged contact. The term "V-shaped terminal aspect" as used herein implies that the terminal aspect has a sharp edge that may be of any angle. The sharp edge contact with the archwire allows for active movement of the bracket. A pin that may be used during early treatment may include an appendage having an active edge also having a sharp edge, such that the sharp edge is located to hold the archwire. This provides a sharp edge contact on either side of the archwire.

In a further aspect of the invention, there is provided a pin adapted for use in an orthodontic appliance according to the invention, the pin adapted to have longitudinal movement within the channel formed between the securing member and the bracket of the orthodontic appliance; and the pin including an appendage having a recess having at least one active surface, the active surface or surfaces being configured to provide, in use, and in conjunction with an archwire, a prescribed force upon a tooth of a patient.

The active surface of the appendage may be varied in shape to create a different shape for the slot, depending upon the movement required for each individual tooth. For example, the active surface may be flat or sharp edged, and/or angled labialy, buccaly, lingualy or palately depending upon the prescribed treatment or arch wire to be used. The pin and bracket arrangement effectively allows positive and negative root torque and other movements to take place on alternate teeth in a specifically designated way and at any time during treatment. The pins may be individualised in a patient to provide a prescribed treatment for each tooth. When a specific designated force requirement is placed upon a tooth, it is preferred to use either a metal, such as steel or titanium, or ceramic facia, if used, as some plastic facias may be subject to distortion.

The recess within the appendage of the pin, in conjunction with the V-shaped aspect of the securing member, forms a slot for the archwire to pass through, to secure the archwire. The pin may be varied during treatment, to change the appendage and alter the dynamics of the pin.

The slot provided between the recess in the appendage of the pin and the bracket allows for rectangular, round and ribbon archwires to be used which allows for individual torque, angulation and rotation movements of every tooth. The degree of movement can be determined for each tooth separately and accurately according to a prescription, and can be either negative or positive depending upon the requirements of each individual tooth.

The pins may be made from any suitable material, but are preferably made from titanium or stainless steel or other metal depending upon the type of movement which is required.

The bracket may be formed of any suitable material, such as metal or ceramics. Most preferably the bracket is stainless steel or titanium. The facia may also be formed of any suitable material such as plastic, ceramic or metal, and be the same or different from the rest of the bracket. The facia does not generally contact the archwire, and may readily be made of ceramic or plastic as it will not be subject to the wear caused by the archwire. In a preferred form, the facia simply slides over the rest of the bracket and it is able to be readily removed and replaced during treatment as necessary.

The facia may be made in such a way that fracture of the facia is unlikely to occur with all aspects of the facia preferably being curved to facilitate soft tissue acceptance. The facia may be made with sufficient depth, without effecting treatment considerations. The archwire is held in the same position to the enamel tooth surface regardless of the depth of the facia, as it is the combination of the bracket and the pin which positions the archwire. Auxiliary holding devices may be used in order to secure the facia if it is necessary to assist in placement of the archwire by drawing the prescribed pin into the bracket slot.

The channel in the bracket acts as a stabiliser for the utilisation of the pin. In order to prevent adhesive from entering the channel, it is preferred to place a plastic prepositioner in the channel of the securing member, which will assist the operator in placing the bracket in exactly the position required and at the same time safeguard against any adhesive material entering the channel and thus preventing the pin from being housed. The bracket may have a guide to assist in placement of the pin. Once the bracket and pin are in position, the facia may be placed over the bracket and complete the channel.

The pins may be formed to provide initial pins and also finishing, rotational, angulation and torquing pins. The pins should be made such that each pin is able to locate securely within the channel formed between the bracket and the securing member. Because the pins are able to fit into the channel and are held with the bracket, the pin cannot rotate and therefore any modification of the appendage of the pin can be utilised to achieve various desirable tooth movements.

By utilising specific pins, it is also possible to obviate the need to use multiple tubes on molars. An appliance may be placed on a molar such that the V-shaped terminal aspect of the bracket faces gingivally or occlusally as desired. A specifically adapted pin where the appendage includes a tube to locate an archwire may then be positioned. The tube may be either round, rectangular or specifically shaped, depending on the archwire used.

In yet a further aspect, the invention provides a method of orthodontic treatment using the orthodontic appliance of the invention including the steps of:

bonding the bracket to the enamel of an individual tooth;

fixing a pin within the channel formed between the securing member and the bracket of said orthodontic appliance, in such a manner that a slot is formed between the V-shaped terminal aspect of the securing member, and the recess and such that the pin is able to retain longitudinal movement; and placing an archwire so that it is secured in the slot formed between the V-shaped terminal aspect and the recess.

During treatment, an appliance according to the invention is affixed to a number of teeth of a particular patient. Each appliance may have the same or a different pin depending on the treatment required.

The following is a description of preferable features of the method, which may be varied depending upon the specific treatment requirements.

In the first stage of treatment, free tipping and rotation of a tooth is enhanced by a point to point contact between the V shaped terminal aspect of the securing member of the bracket and active surface of the pin. In this initial stage, the active surface of the pin may be sharp. The pin is firmly locked into position as it is located between the bracket and the securing member and no rotation of the pin may occur however the pin may move longitudinally. This allows for rotation and angulation of the tooth.

It is envisaged that during the first stage of treatment, a round wire may be used, and a finishing wire may be used at the end of the treatment. Angulation and rotation of teeth can also be achieved by auxiliary wires which are utilised in such a way that a first order leverage is used in both instances. The angulation pins and the brackets allow a transition of leverage to occur from second, third and then to first order leverage.

Such movement will be achieved by the utilisation of the first order of leverage whereby the fulcrum is the center of the bracket and the applied rotational or angulation force applied to the main archwire on both the mesial and distal of the bracket. The result is that less auxiliary components are required with a 50% force requirement on each side of the bracket. The result is a much less complex but more dynamic movement. The tooth can move in all three dimensions at the one time. Currently used auxiliaries may however be utilised with the appliance of the invention and may be modified in order to be used in the new appliance system.

The bracket may also incorporate small holes in the mid section of the securing member to allow ligation of severely displaced teeth. Once such displaced teeth are drawn to the main archwire, the formation of the channel may be achieved by the placement of the facia over the securing member, or placing the pin within the appliance.

Torquing can be achieved using ordinary torquing auxiliaries as used in the existing techniques if desired and therefore the finishing procedure may be achieved using current principles. It is preferred that treatment procedures be commenced in light round wires and finishing can be achieved in either round, rectangular or ribbon archwires.

The archwire height does not need to be changed during treatment as may be the case in existing combination brackets. The appliance of the invention is able to individually root torque all teeth including premolars in the finishing stage. Furthermore, the torque is controlled to the exact degree by the specific active surfaces of the pins that are utilised with the appliance.

The appliance of the invention may be used both in an inverted or upright position during any stage of the aforementioned technique, so that the pin appendage may face in the gingival or occlusal direction. The appliance may be applied to teeth in any prescribed manner, including labialy, buccaly, lingually and palately.

The method also involves the use of brackets that include a pin where the appendage forms a tube adapted to secure the archwire in position. The pin is designed for use on the molars of a patient. A plurality of different tube pins may be used during the treatment of a patient to accommodate variations in the archwire used. For example, the tube pin may be replaced when the archwire is changed from a round wire to a rectangular or ribbon wire. It is envisaged that this method of providing molar tubes may be used in other techniques and conventional brackets. The tubes are easily interchanged during treatment to the desired configuration, simply by slipping a new tube pin into the molar bracket.

An advantage is that in most instances, only one or at most two molar tubes need to be used on each molar tooth. The occlusal plane does not vary as the archwire remains in the same position throughout the treatment. This differs from present utilisation of combination brackets where there is a need to change the position of the archwire during finishing in order to engage the horizontal bracket channel and combination tubes on molar teeth.

An advantage achieved by the bracket of the invention in general use, is that the archwire is held close to the enamel surface of the tooth. This is achieved by the formation of the slot between the recess in the pin and the bracket to hold the archwire. The archwire is held in the same position in relation to the tooth.

A further advantage is that the contact between the archwire and the bracket is a metal to metal contact at all stages.

A further advantage is that the facia, if present, may be readily changed without the necessity to remove the bracket from the tooth, which provides aesthetic benefits. The facia can be changed from ceramic to plastic and to metal during treatment and even differing colours may be utilised by simply removing the facia from the rest of the bracket and replacing it with a different facia. There is no need to debond the bracket in order to change the facia.

A further advantage of the bracket, is the unique sharp terminal aspect formed in the securing member of the bracket. This forms a knife edge connection with the archwire which allows the operator to control the torque of the tooth for precision of movement. The bracket of the invention has the ability to torque accurately individual teeth, both premolars and anterior teeth, the teeth can be torqued individually and separately and at the same time. The teeth can also be angulated and rotated in a precise and individual manner and at the same time.

A further advantage is that the torque and indeed angle may be varied during treatment, by changing the pin. In prior art appliances, torque is generally determined by the fixed bracket geometry. Therefore, it is either difficult, or not possible to vary the bracket torque during treatment.

A further advantage is that the teeth may be precisely moved in a prescribed manner individually and collectively. An operator may simply prescribe a particular pin in order to effect the correct treatment.

A further advantage is the smoothness of the bracket which adds to the comfort of the patient. As the archwire is held at a constant distance to the enamel surface on all the teeth, treatment procedures are enhanced and simplified.

The present invention will now be described with reference to the accompanying drawings. It should be understood that these drawings are merely illustrative of preferred embodiments of the invention, and the scope should not be considered to be limited thereto.

FIG. 2 is a top view of the same embodiment, while

FIG. 5 is a perspective view of a facia in accordance with the present invention. FIG. 6 is a top view of the same embodiment while FIGS. 7 and 8 are side and end views respectively.

FIG. 11 is a perspective view of a further pin in accordance with the present invention, while FIG. 12 is a side view of the same embodiment.

FIG. 14 is a top view of the same embodiment, while

FIG. 17 is a perspective view of a further pin in accordance with the invention. FIG. 18 is a top view of the same embodiment, while FIGS. 19 and 20 are a side and end view respectively.

FIG. 22 is a top view of the same embodiment, while

FIG. 26 is a top view of the same embodiment, while

FIG. 30 is a top view of the same embodiment, while

FIG. 33 is an exploded view of a bracket, facia and pin in combination.

Figure 3:
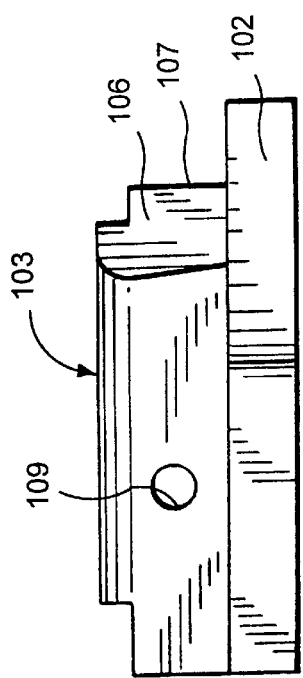
FIGS. 3 and 4 are side and end views respectively.
Figure 4:
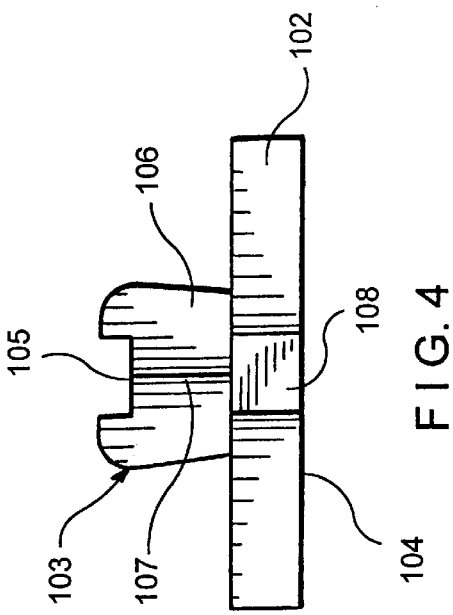
Figure 1:
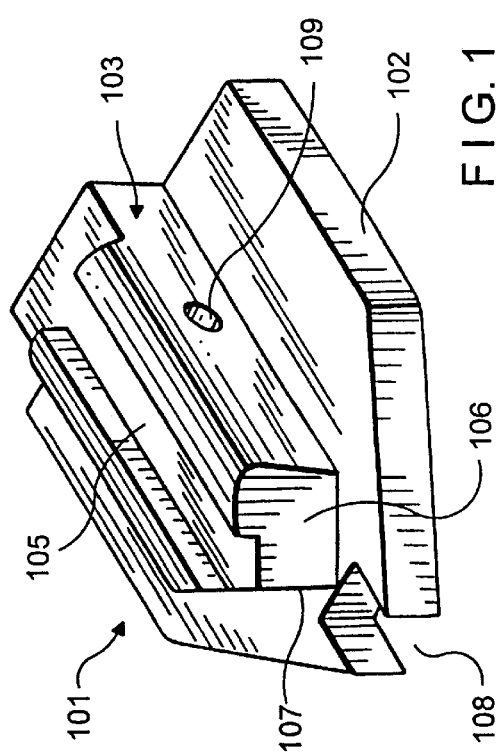
FIG. 1 illustrates a perspective view of a bracket according to the first embodiment of the invention (without the facia) in accordance with the invention.
Figure 2:
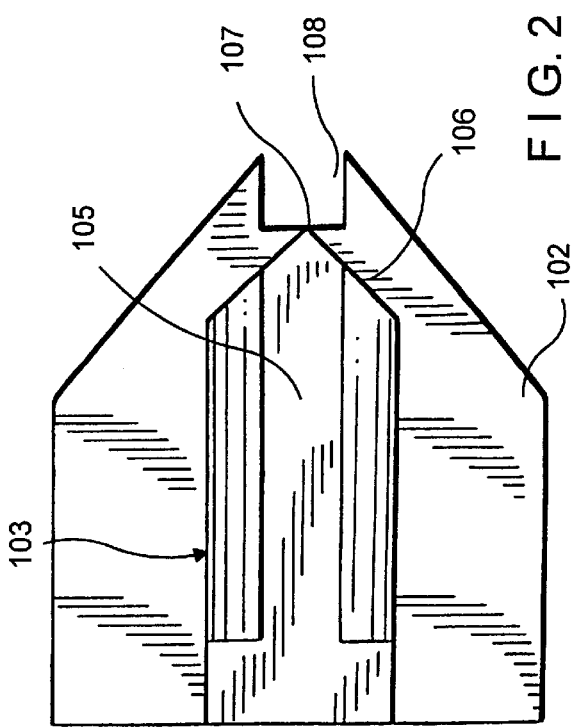

FIGS. 1 to 4 illustrate a bracket (101) (without a facia) having a base (102) and a securing member (103). The base has a flat surface (104), the securing member being positioned opposite the flat surface. The securing member has a central channel (105) culminating in a V-shaped terminal aspect (106). The V-shaped terminal aspect produces a sharp edge (107).

The base of the bracket may include a terminal recess (108) for engaging the appendage of a pin in order to assist in securing a pin to the bracket. A ligature hole (109) is positioned in the securing member and may be used if the treatment so requires.

FIGS. 5 to 8 illustrate a facia (110) which includes a securing sleeve (111) which is able to surround the securing member (103) of the bracket. The securing sleeve is adapted to slide over the securing member. A central groove (112) is located in the facia, which in combination with the groove (105) of the bracket forms a channel when the facia is secured over the bracket, which is shaped to secure the pin. The pin may still have longitudinal movement through the channel. The facia also includes a terminal recess (113) into which the heel of a pin may locate assisting in securing both the pin and the facia. The facia has a smooth outer surface (125) which aids the comfort of the patient.

Figure 10:
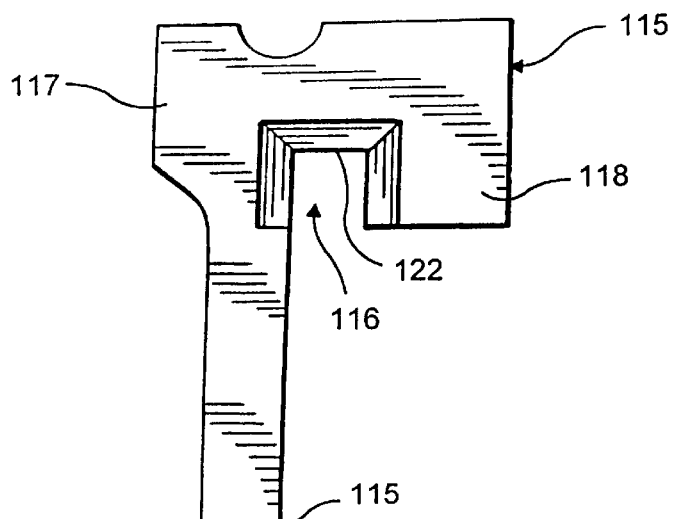
FIG. 10 is a side view of the same embodiment.
Figure 9:
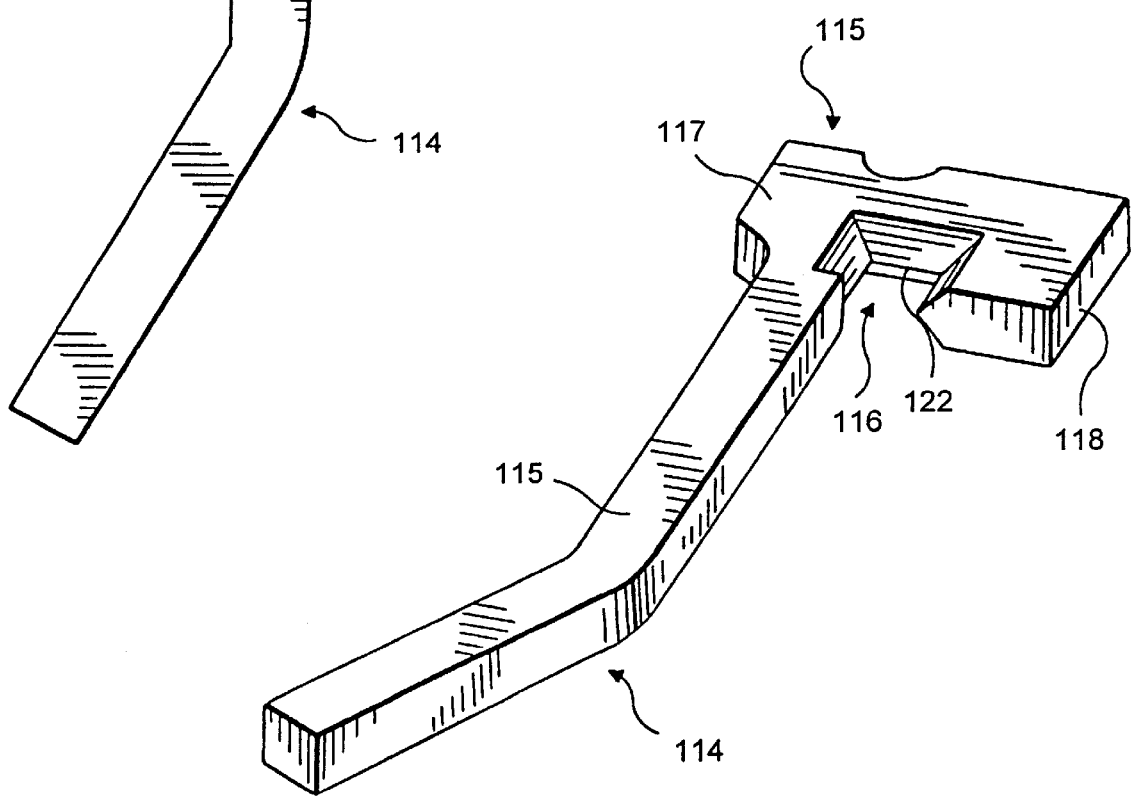
FIG. 9 is a perspective view of a pin in accordance with the present invention, whilst

FIGS. 9 and 10 illustrate a torqueing pin (114) in accordance with the invention having a stem (115) which is able to locate within the channel formed between the facia and the bracket. The stem (115) is shaped specifically to locate firmly within the channel but may still move longitudinally. The appendage of the pin has a recess (116) with a sharp edge (122). The recess (116) in conjunction with the V-shaped aspect (106) of the securing member forms a slot through which an archwire may be passed. The appendage includes a heel (117) which is able to position in the terminal recess (113) of the facia while toe (118) is able to secure into the terminal recess (108) of the bracket.

The pin itself is held securely between the securing member of the bracket and the facia and is unable to rotate as it has the same cross sectional dimension to the slot. It may however have longitudinal movement.

Figures 11, 12:
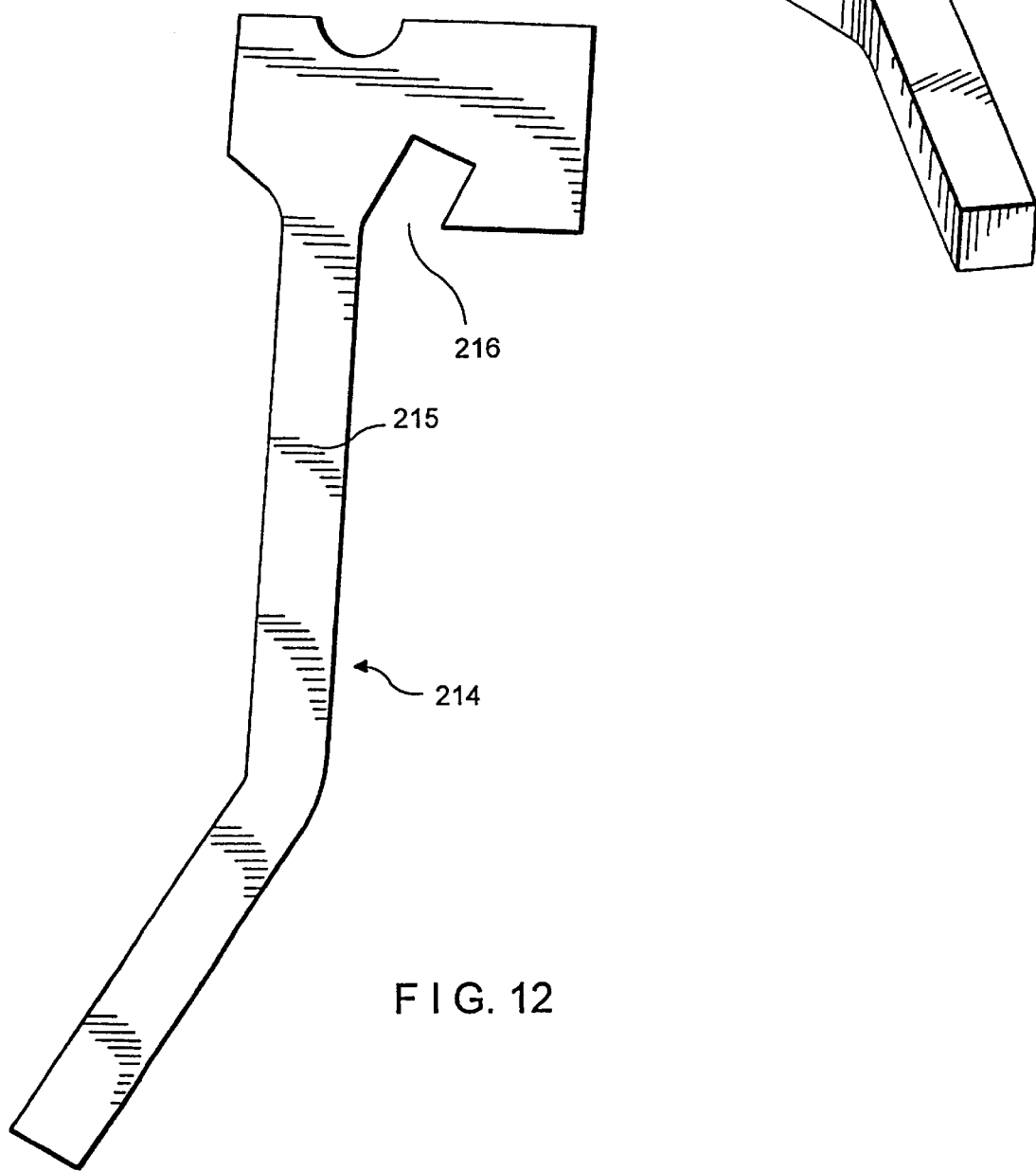
Figure 16:
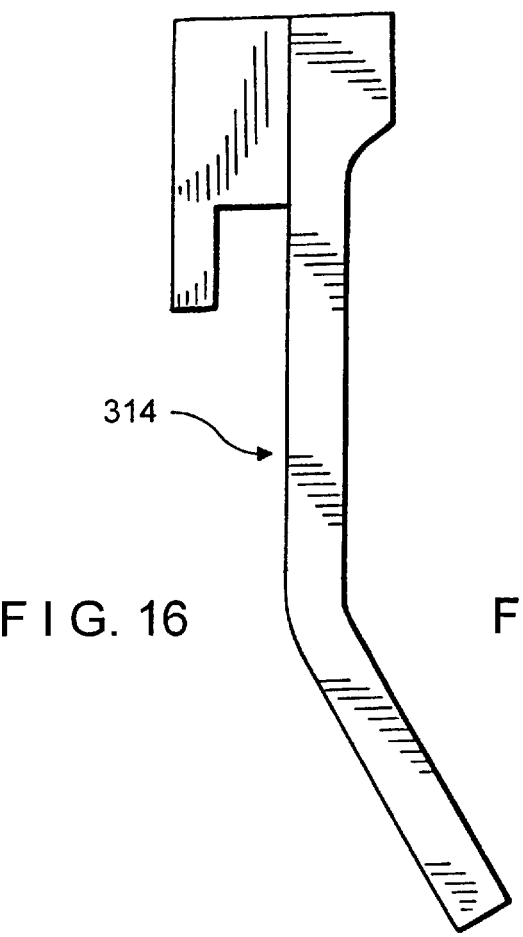
FIGS. 15 and 16 are a end and side view respectively.
Figure 14:
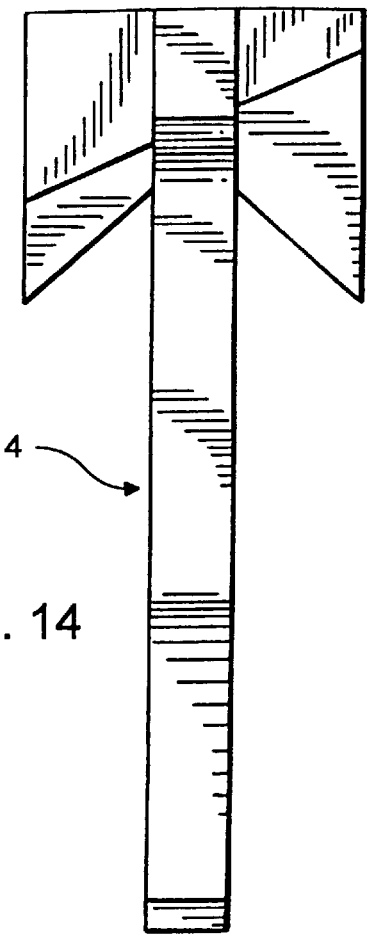

FIGS. 11 and 12 illustrate an alternative pin (214) wherein the active surface of the recess (216) is rectangular shaped and angled so as to provide torque for a particular tooth movement.

Figure 13:
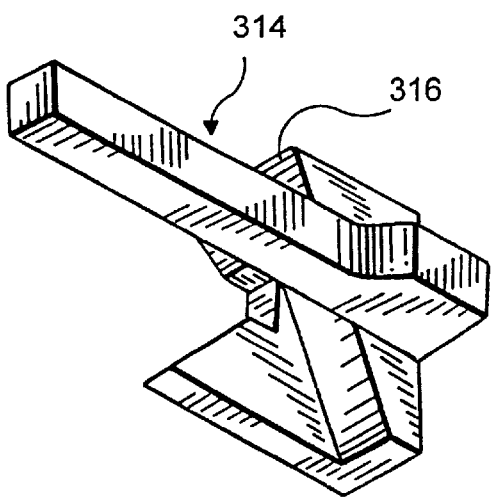
FIG. 13 is a perspective view of a further pin in accordance with the invention.
Figure 15:
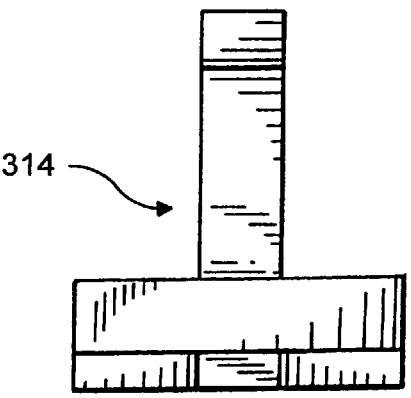
Figure 21:
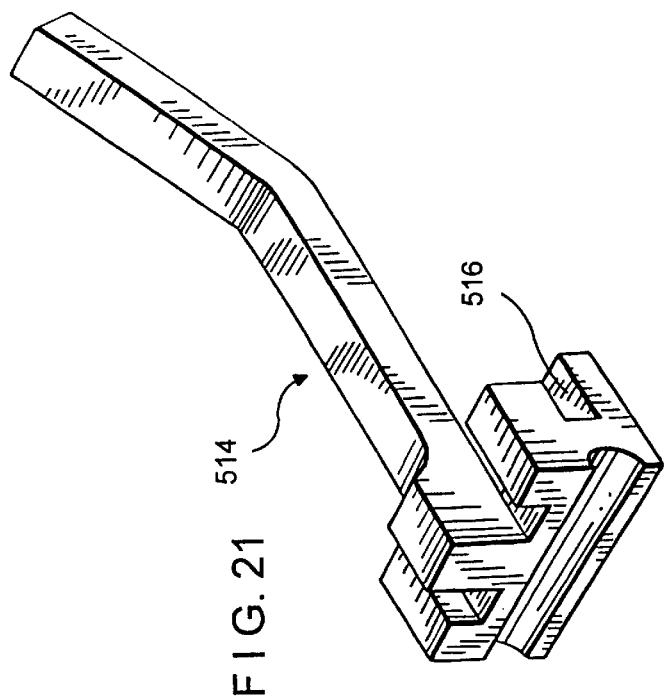
FIG. 21 is a perspective view of a further pin in accordance with the invention.
Figure 24:
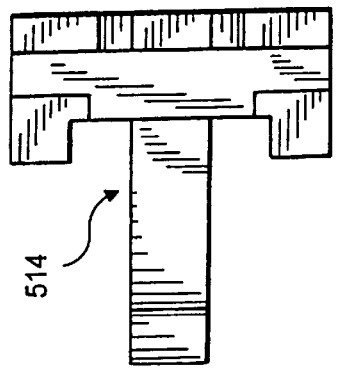
FIGS. 23 and 24 are a side view and end view respectively.
Figure 23:
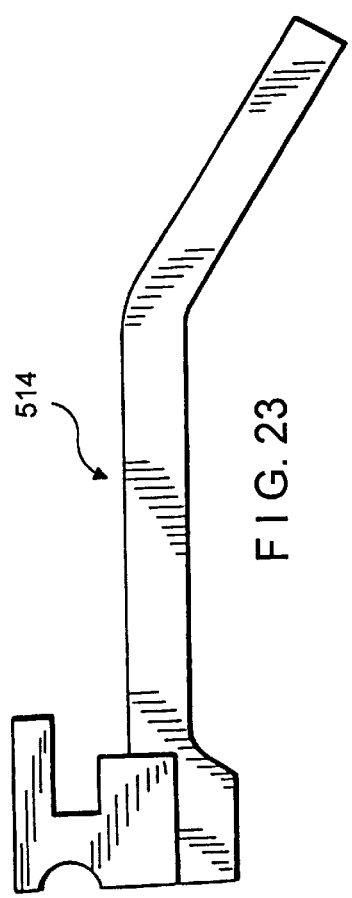
Figure 22:
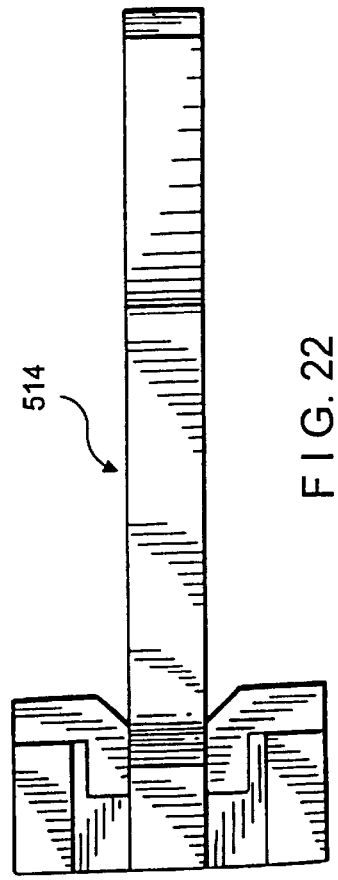
Figure 28:
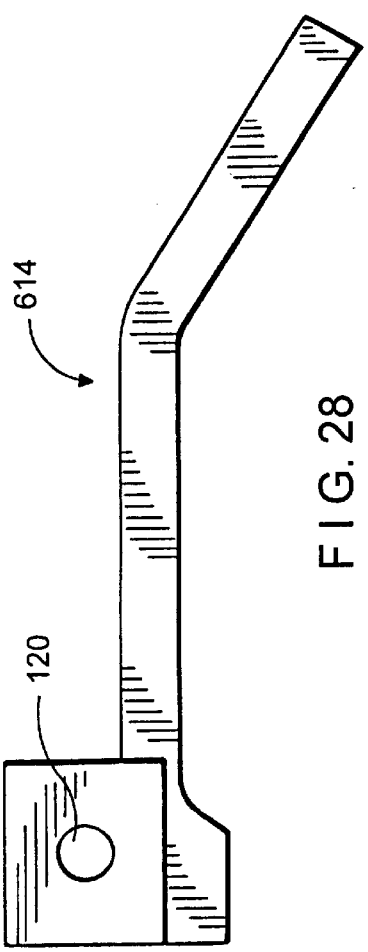
FIGS. 27 and 28 are a end view and side view respectively.
Figure 26:
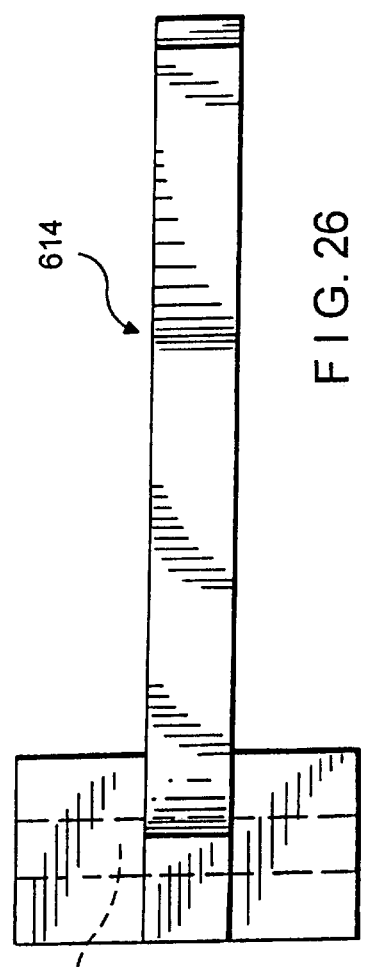

FIGS. 13 through to FIG. 24 illustrate various other embodiments of pins (314, 414 and 514 respectively) wherein the appendage, and in particular the active surfaces of the recess located in each pin varies depending upon the treatment required for a particular tooth. The angle of the active surface (316, 416 and 516 respectively) varies the uprighting force applied to each tooth. Each pin is able to locate and be secured within the slot between the securing member and the facia.

Figure 25:
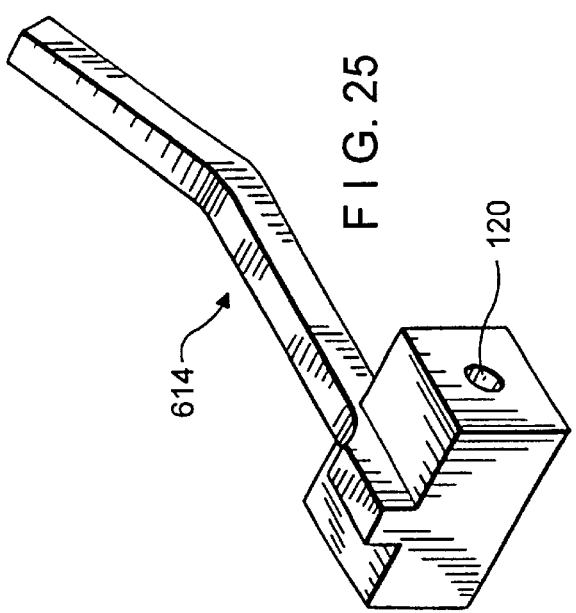
FIG. 25 is a perspective view of a pin in accordance with the invention which may be used for a molar tube.
Figure 27:
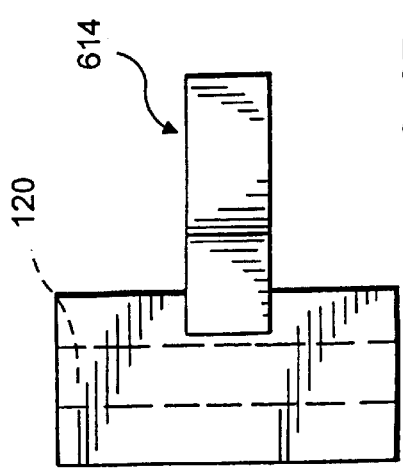
Figure 30:
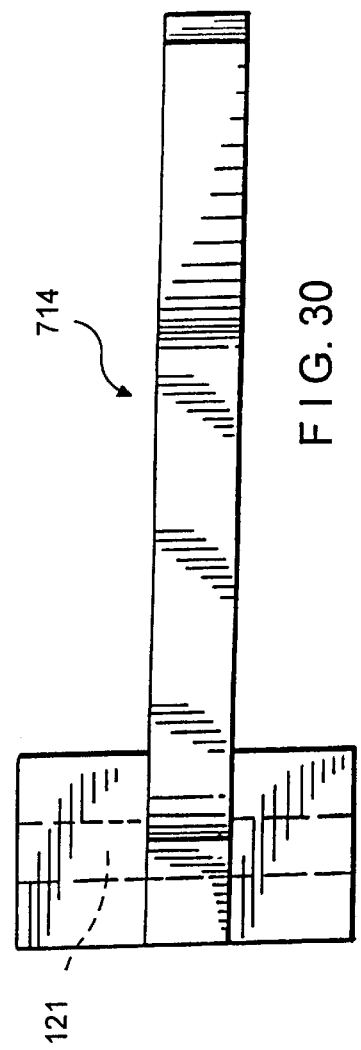
Figure 32:
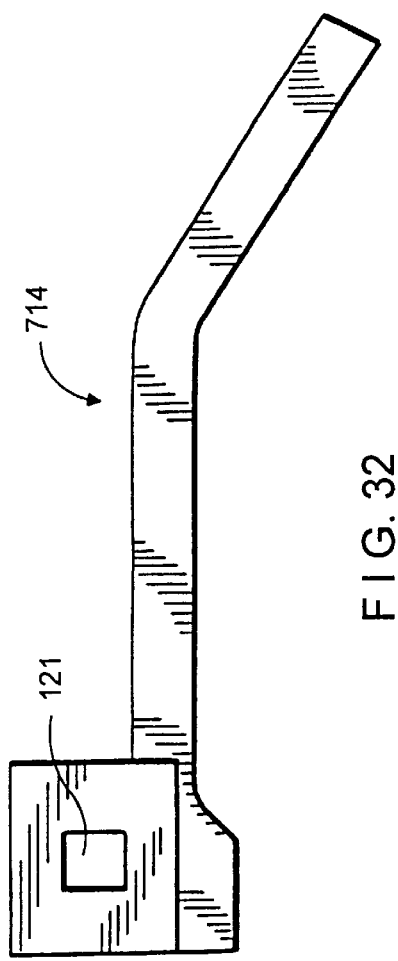
FIGS. 31 and 32 are an end and side view respectively.
Figure 31:
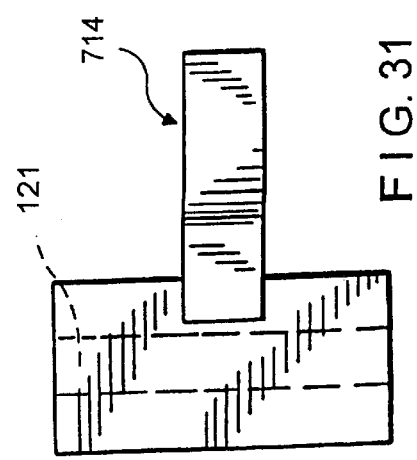

FIGS. 25 and 32 illustrate embodiments of a pin (614 and 714 respectively) that may be used as a molar tube. The pins may be used occlusally where the bracket is placed such that the V-shaped edge of the bracket faces gingivally, or the pins may be used gingivally depending on positioning of brackets.

Figure 29:
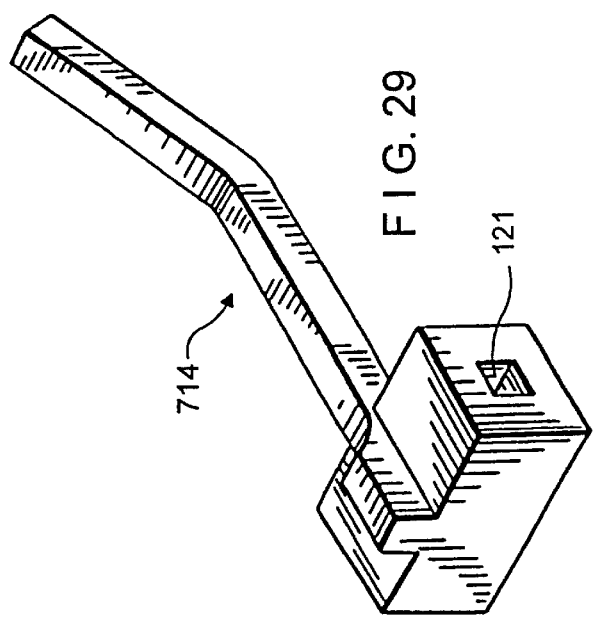
FIG. 29 is a perspective view of a further pin in accordance with the invention which may also be used as a molar tube.
Figure 35:
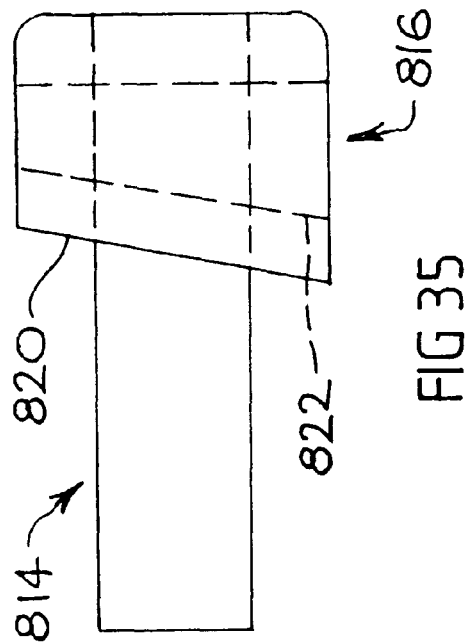
FIG. 35 is a pin suitable for the bracket of FIG. 34.

When the pin of FIG. 25 or 29 is located within a bracket in such a position, the need for multiple tubes to be used, as in current techniques is eliminated. The archwire remains at the same level during treatment and both round archwires (FIG. 25) and rectangular archwires (FIG. 29) are able to be slotted into tubes (120) or (121) respectively. The use of the bracket and the particular pin eliminates the need as in current techniques to use expensive or multiple tubes on molars.

FIG. 33 illustrates an exploded view with bracket (101), facia (110) and pin (114) all in appropriate relation to each other. The facia is able to slide over the securing member (103) of the bracket to form a channel within the bracket. The pin is able to be secured within the channel formed by the facia and the securing member in such a manner that it is unable to rotate. An archwire (not illustrated) is able to be located within the slot formed between the recess (116) of the appendage of the pin and the sharp edge (107) of the bracket.

Figure 34:
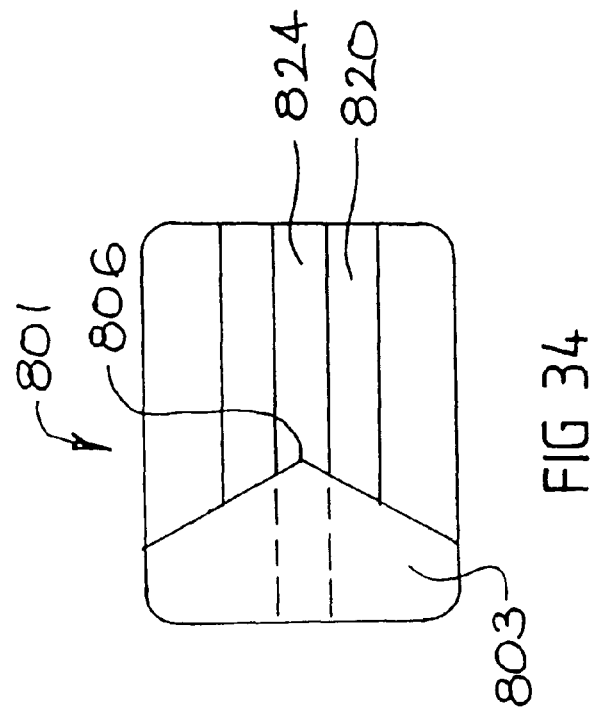
FIG. 34 is a top view of a bracket and securing member according to the second embodiment of the invention.

FIG. 34 illustrates a top view of a bracket (801) according to the second embodiment of the invention wherein the securing member (803) is integral with the base. The V-shaped terminal aspect (806), in use faces occlusally. The pin (814) with appendage (816) is able to slide within channel (820). The appendage abuts against the V-shaped terminal aspect (806) at surface (820). A slot is formed between the V-shaped terminal aspect, and an active surface (822) of the appendage. The active surface of the appendage may be angled to provide either or both torque and angulation forces to the tooth. An archwire (not shown) may be positioned within the slot formed between the V-shaped terminal aspect and the appendage.

Channel (820) is "T" shaped to provide a central auxiliary channel (824) for placement of a spring (not shown). The spring may be placed to hold firmly the pin, with the coils located around the stem of the pin. A hook may then extend through the auxiliary channel for placement over the occlusal end of the appendage. The spring acts to drive the appendage of the pin against the V-shaped terminal aspect.

Figure 36:
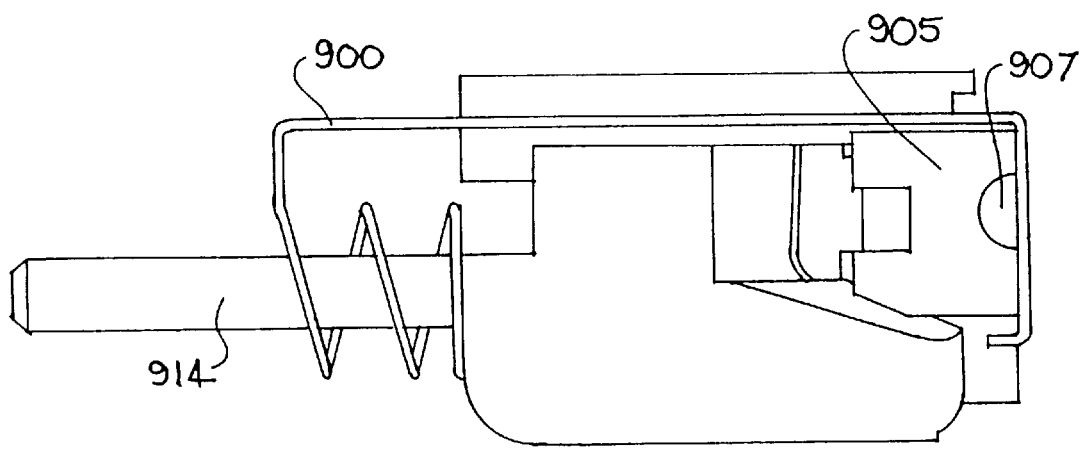
FIG. 36 shows a side elevation of a pin held in position by a spring auxiliary.

FIG. 36 illustrates a spring (900) positioned with the coils around the stem (914) of the pin. A hook is placed through the auxiliary channel to draw the appendage toward the V-shaped terminal aspect. Alternatively, an elastic may be placed around auxiliary groove (907) and fitted around the back of the stem of the pin.

Figure 37:
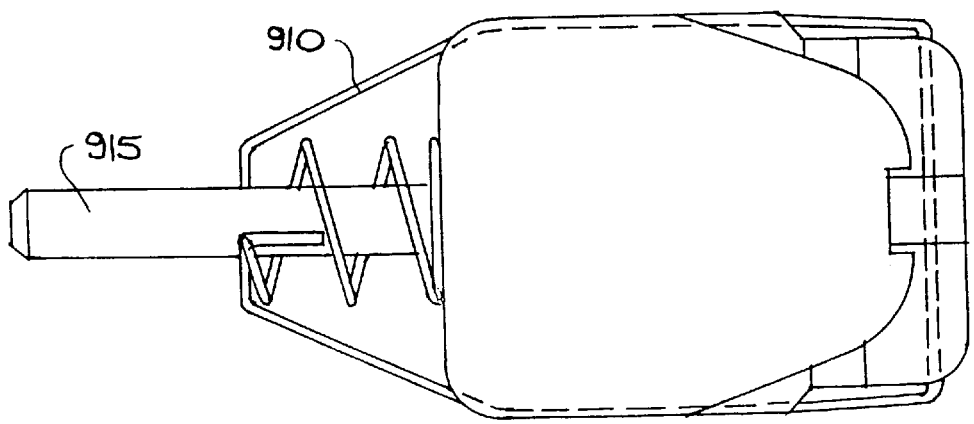
FIG. 37 shows a top view of an appliance with an alternative spring arrangement.

FIG. 37 shows an arrangement where the pin is held in position by an alternative auxiliary spring arrangement (910). In this arrarngement, the hook portion of the spring is placed around the outside of the appliance and through the auxiliary groove in the appendage of the pin. The coil is placed around the stem (915) of the pin.

It should be understood that the above description is merely illustrative of the present invention, and any modification without departing from the spirit or ambit of the invention is also to be included herein.

What is claimed is:

1. An orthodontic appliance comprising:
   a bracket having a substantially flat base for engaging a tooth,
   a securing member having a V-shaped terminal aspect,
   a facia, able to engage with the securing member to form part of the bracket;
   a pin having a stem and an appendage including a recess having an active surface; and
   an auxiliary means associated with the pin,
   wherein the combination of the facia and the securing member form a channel within the bracket, able to secure the pin in a position to retain longitudinal movement and where a slot is formed between the V-shaped terminal aspect and the recess of the pin, and
   said auxiliary means urging longitudinal movement of said pin within the channel, to vary the dimensions of the slot formed between the V-shaped terminal aspect and the recess of the pin.

2. An orthodontic appliance according to claim 1, wherein the securing member forms a tongue arrangement that is compatible with a groove within the facia, and so formed that when the facia is placed over the securing member, said channel is formed between the facia and the securing member.

3. A pin adapted for use in an orthodontic appliance according to claim 1 or 5, said appliance having said securing member and said bracket forming said channel between the securing member and bracket;
   said pin having a stem adapted for longitudinal movement within the channel; and
   said pin including an appendage having a recess having an active surface, said active surface being configured to provide, in use, and in conjunction with an archwire, a prescribed force upon a tooth of a patient wherein, the angle of the active surface relative to the archwire is altered following longitudinal movement to the pin.

4. A pin according to claim 3, wherein the prescribed force is torque, angulation and/or rotation.

5. An orthodontic appliance comprising:
   a bracket having a substantially flat base for engaging a tooth,
   a securing member having a V-shaped terminal aspect,
   a pin having a stem and an appendage including a recess having an active surface; and
   an auxiliary means associated with the pin,
   wherein the base and the securing member form a channel, able to secure the pin in a position to retain longitudinal movement and where a slot is formed between the V-shaped terminal aspect and the recess of the pin, and
   said auxiliary means urges longitudinal movement of said pin within the channel, to vary the dimensions of the slot formed between the V-shaped terminal aspect and the recess of the pin.

6. An orthodontic appliance according to claim 5, wherein the active surface of the recess of the pin faces gingivally and the V-shaped terminal aspect of the securing member points occlusally;
   said pin further including an auxiliary groove on the occlusal surface of the appendage; and
   said orthodontic appliance includes an auxiliary channel running longitudinally between the pin and the flat base for placement of one or more auxiliaries.

7. An orthodontic appliance according to claim 6, wherein said auxiliary means comprises an elastic or a spring which affixes around the auxiliary groove of the pin through the auxiliary channel and around either the stem of the pin or the bracket and acts to urge the pin in a gingival direction toward the V-shaped terminal aspect.

8. An orthodontic appliance according to claim 1 or 5 wherein, in use, an archwire is secured within the slot formed between the V-shaped terminal aspect of the securing member and the recess of the pin.

9. An orthodontic appliance according to claim 8, wherein the active surface of the recess of the pin, in conjunction with the archwire, in use, applies a prescribed force to a tooth of a patient.

10. An orthodontic appliance according to claim 9, wherein the prescribed force applied to a tooth is torque, angulation, and/or rotation.

11. An orthodontic appliance according to claim 1 or 5, wherein the bracket includes a guide to assist in the placement of the pin.

12. An orthodontic appliance according to claim 1 or 5, wherein the appliance includes a plurality of pins having differing active surfaces, wherein, in use, a pin may be removed without the need to debond the bracket and replaced with an alternative pin depending on the type of force to be applied to the tooth of a patient in use.

13. An orthodontic appliance according to claim 1 or 5 wherein the pin and the channel have substantially the same cross sections.

14. A method of orthodontic treatment using an orthodontic appliance, said orthodontic appliance having:

a bracket having a substantially flat base for engaging a tooth;

a securing member having a V-shaped terminal aspect, a facia able to engage with the securing member to form part of the bracket; and a pin having an appendage including a recess having an active surface; said method including the steps of:

bonding the bracket to the enamel of the tooth;

fixing the pin within a channel formed between the facia and the securing member of said orthodontic appliance in such a manner that the pin retains longitudinal movement and a slot is formed between the V-shaped terminal aspect and the recess of the pin;

placing an archwire so that it is secured in the slot formed between the V-shaped terminal aspect and the recess of the pin; and affixing an auxiliary means in association with the pin to urge longitudinal movement of the pin within the channel to vary the dimensions of the slot formed between the V-shaped terminal aspect and the recess of the pin.

15. A method of orthodontic treatment using an orthodontic appliance, said orthodontic appliance including:

a bracket having a substantially flat base for engaging a tooth;

a securing member having a V-shaped terminal aspect; and a pin having an appendage including a recess having an active surface; said method including the steps of:

bonding the bracket to the enamel of an individual tooth;

fixing the pin within a channel formed between the securing member and the bracket of said orthodontic appliance, in such a manner that the pin retains longitudinal movement and a slot is formed between the V-shaped terminal aspect and the recess of the pin;

placing an archwire so that it is secured in the slot formed between the V-shaped terminal aspect and the recess of the pin, and affixing an auxiliary means in association with the pin to urge longitudinal movement of the pin within the channel, to vary the dimensions of the slot formed between the V-shaped terminal aspect and the recess of the pin.

16. A method according to claim 14 or 15, wherein during treatment the pin and/or the archwire may be removed without the need to debond the bracket, and replaced depending upon the treatment required for that tooth.

17. A method according to claim 16, wherein the orthodontic appliance is placed so that a stem of the pin points in the gingival direction and the appendage of the pin points in the occlusal direction.

18. A method according to claim 17, wherein the pin is formed with an auxiliary groove on the occlusal surface of the appendage of the pin and the orthodontic appliance is formed with an auxiliary channel running longitudinally between the pin and the flat base; and said auxiliary means is affixed around the auxiliary groove of the pin through the auxiliary channel and around either the stem of the pin or the bracket, to urge the pin in a gingival direction toward the V-shaped terminal aspect.

19. A method according to claim 14 or 15, wherein the active surface of the recess of the pin, in conjunction with the archwire applies a prescribed force upon a tooth of a patient.

20. A method according to claim 19, wherein a resultant longitudinal movement of the pin varies the prescribed force upon the tooth.

21. A method according to claim 19, wherein the prescribed force applied to the tooth is torque, angulation and/or rotation.

22. A method according to claim 14 or 15, wherein the appliance is applied to the tooth in a labialy, buccaly, lingually or palately manner.

23. A method according to claim 14 or 15, wherein a specifically adapted pin is used on an appliance fixed to a molar tooth, said specifically adapted pin being formed as a tube able to locate an archwire in said tube when in position.

* * * * *